United States Patent [19]

Takazawa et al.

[11] Patent Number: 5,443,968
[45] Date of Patent: Aug. 22, 1995

[54] FED BATCH CULTURE METHOD FOR PROTEIN SECRETING CELLS

[75] Inventors: Yoshiharu Takazawa; Seiichi Yokoyama, both of Hino, Japan

[73] Assignee: Teijin Limited, Osaka, Japan

[21] Appl. No.: 170,361

[22] PCT Filed: Apr. 30, 1993

[86] PCT No.: PCT/JP93/00586

§ 371 Date: Jan. 3, 1994

§ 102(e) Date: Jan. 3, 1994

[87] PCT Pub. No.: WO93/22448

PCT Pub. Date: Nov. 11, 1993

[30] Foreign Application Priority Data

May 1, 1992 [JP] Japan .................................. 4-112653

[51] Int. Cl.$^6$ .......................... C12N 5/08; C12P 21/00
[52] U.S. Cl. ............................. 435/70.3; 435/240.25; 435/240.2
[58] Field of Search ................. 435/70.3, 240.25, 240.2

[56] References Cited

U.S. PATENT DOCUMENTS 5,219,752 6/1993 Takazawa ......................... 435/70.3
5,328,844 7/1994 Moore ............................. 435/240.31

FOREIGN PATENT DOCUMENTS 0136053 4/1985 European Pat. Off. .
0215548 3/1987 European Pat. Off. .
0319944 6/1989 European Pat. Off. .
0343635 11/1989 European Pat. Off. .

OTHER PUBLICATIONS

Journal of Immunological Methods, 86 (1986) pp. 61–69, "Comparison of cell propagation methods for their effect on monoclonal antibody yield in fermentors" S. Reuveny et al.

*Primary Examiner*—Herbert J. Lilling
*Attorney, Agent, or Firm*—Wenderoth, Lind & Ponack

[57] ABSTRACT

In a process of production of a useful protein by culturing a human embryonal kidney cell-derived 293 strain which is introduced with a useful protein-expressing gene, it becomes possible to obtain a culture fluid containing the useful protein in a high concentration using an extremely small amount of the medium, by carrying out a fed-batch culture and adding a sugar or a sugar and a calcium in a specified stage of the culture.

24 Claims, 6 Drawing Sheets

FED BATCH CULTURE METHOD FOR PROTEIN SECRETING CELLS

BACKGROUND OF THE INVENTION

1. Field of the Invention

This invention relates to a process for the production of a useful protein by making cells secrete the useful protein. More particularly, this invention relates to a process which comprises culturing a human embryonal kidney-derived 293 cell transformed so as to express a useful protein to obtain a culture fluid containing the desired useful protein in a high concentration, and recovering the useful protein from the culture fluid.

2. Description of Related Art

Production of useful proteins, particularly physiologically active proteins by culturing animal cells, is widely carried out. Particularly, processes of producing useful proteins by culturing animal cells transformed so as to secrete the useful proteins are indispensable techniques for production of certain useful proteins.

Animal cells are superior to bacteria and yeasts in the ability of post-translational modification. However, when animal cells are used, the cost of the medium and purification are relatively high due to a low product concentration in culture fluid. Therefore, it is important for industrial production to raise the concentration of useful proteins secreted by animal cells. In a simple batch culture method, proliferation of the cells stops at some point of the culture period mainly due to the exhaustion of nutrients, and secretion of the protein also stops. In order to improve this simple batch culture method, a so-called fed-batch culture method is carried out in which exhausted nutrients, for example sugars, amino acids or a fresh medium, are added continuously or intermittently during the culture period.

In this specification, a "simple batch culture method" means a method which comprises inoculating cells into a medium in a culture vessel to start culture, and carrying out the culture without substantial addition of part or all of the nutrients or a new medium until completion of the culture, and a "fed-batch culture method" means a method comprising inoculating cells into a medium in a culture vessel to start culture, and carrying out the culture while adding part or all of the nutrients or a fresh medium continuously or intermittently into the culture vessel, without substantially taking out the culture fluid from the culture vessel.

It is known that in a fed-batch culture method, the culture period is prolonged and higher cell density and product (protein) concentration can be obtained compared to a simple batch culture method (J. B. Griffith, Animal Cell Culture and Production of Biologicals, pp. 401–410, Klumer Academic Publishers, R. Sasaki and K. Ikura (eds.), (1991), S. Reuveny et al., J. Immunol. Methods, 86, 53 (1986), S. Reuveny et al., J. Immunol. Methods, 86, 61 (1986)). In the above literature of J. B. Griffith, a comparison shown in the following Table 1 is given as a typical example.

TABLE 1

| Culture type | Number of cells (millions) | Product yield (mg/week) | Per liter (mg/month) | Length (days) |
| --- | --- | --- | --- | --- |
| Batch | 3 | 100 | 200 | 7 |
| Fed batch | 6 | 200 | 500 | 14 |

The above S. Reuveny et al. compares a simple batch culture with a fed-batch culture in the latter of the above literatures. This comparative experiment has been conducted under the following conditions: (1) The simple batch culture comprised inoculating hybridoma cells at a density of $3 \times 10^5$ cells/ml in 100 ml of a medium and carrying out culture for 8 days, and (2) the fed-batch culture comprised inoculating hybridoma cells at a density of $3 \times 10^5$ cells/ml in 60 ml of a medium, and then carrying out the culture for 8 days while adding 6 ml of a fresh medium once a day after the density had become about $1 \times 10^6$ cells/ml 2 days after inoculation. The results show that the antibody productivities in both methods are 15 mg/l/day and 27 mg/l/day, respectively. Thus, S. Reuveny et al. teaches an about 1.8-fold increase of the productivity (antibody) in the fed-batch culture compared to the simple batch culture.

Thus, in a fed-batch culture method, cell density and protein concentration can be increased compared to a simple batch culture method. However, in view of medium costs, it is preferable that cell proliferation is rather suppressed at a certain stage and a high productivity of protein is maintained for a long time. In a fed-batch culture method, much energy tends to be consumed for cell proliferation. Therefore, if it is possible to suppress cell proliferation after the sufficient cell growth and to direct energy to the production of the substance (protein), the protein concentration thereof in the culture fluid becomes further higher. However, an inexpensive and effective process has not been reported yet.

On the other hand, EP 0343635A2 discloses a process in which calcium ion concentration in the culture fluid is maintained at a low concentration from 0.002 to 0.3 mM in a process to culture an adherent animal cell line such as human embryonal kidney cell-derived 293 cell, the hamster-derived BHK cell, the hamster-derived CHO cell or a transformant thereof continuously in a serum-free medium in a suspension state. This process is a process to carry out continuous culture in which such adherent animal cells are maintained in a suspension state by maintaining the calcium ion concentration at the above low level, and is a so-called perfusion-suspension culture method which comprises continuously or intermittently supplying a fresh medium into the culture vessel and taking out the spent medium from the culture vessel. Thus in this process, although it is possible to culture adherent cells at a high density and in a suspension state for an extremely long period, it is difficult to accumulate a useful protein secreted by the cells in a high concentration, and the medium cost to produce the useful protein tends to be considerably high.

SUMMARY OF THE INVENTION

The first object of this invention is to provide an improved process of culturing a 293 strain transformed so as to secrete a desired useful protein in a suspension state according to a fed-batch culture method.

The second object of this invention is to provide a process of a fed-batch culture method which comprises proliferating the cell strain at the initial stage, suppressing substantial proliferation of the cells after the cell density has reached a certain level, and thereafter, continuing the production of the useful protein by maintaining the culture for a long period.

The third object of this invention is to provide a process of a fed-batch culture method in which medium consumption in the production of a certain amount of the useful protein is reduced, namely a process wherein medium costs are saved.

The fourth object of this invention is to provide a process which comprises culturing the cell strain in a suspension fed-batch culture stably for a long period to obtain a culture fluid containing a useful protein accumulated in a high concentration.

Another object of this invention is to provide an industrial process to obtain a culture fluid containing a useful protein in a high concentration such that the useful protein can be separated efficiently.

Still another object of this invention is to provide a culture process for obtaining the culture fluid containing Protein C, activated Protein C, or a physiologically active protein having similar activity to them in a high concentration.

Still other objects of this invention will become apparent from the following description.

As a result of intensive research, the present inventors have found that the objects and advantages of this invention can be achieved by a process of production of a useful protein by culturing mammalian cell in a suspension state, wherein the improvement is in that the mammalian cell is a human embryonal kidney cell-derived 293 strain which is introduced with a useful protein-expressing gene, and in that the process comprises (a) starting the culture at a cell density of $5 \times 10^4$ to $5 \times 10^5$ cells/ml, (b) adding a sugar in a culture vessel to give a concentration of 1 to 7 g/l at any time after the cell density in the culture vessel has become three times higher than the inoculum cell density and when the cell density is in a range of $5 \times 10^5$ to $5 \times 10^6$ cells/ml, (c) continuing the culture until the substantial increase of the concentration of the useful protein does not come to be recognized while the suppression of the substantial lowering of the pH of the culture fluid is maintained, and then stopping the culture, and (d) taking out the culture fluid from the culture vessel and recovering the useful protein from the culture fluid.

In the process of this invention, at least 6 to 7-fold higher product concentration compared with a simple batch culture without adding a sugar can be accomplished by selecting a transformed 293 strain and adding a certain amount of a sugar in a certain stage of the culture. Further, even in comparison with a method in which a fresh medium is added additionally in the middle of culture, as is usually put into practice in a fed-batch culture method, a useful protein can be obtained in a several fold larger amount in the process of this invention.

Although the reason is not clear, this phenomenon is surmised to be attributed to the inherent character of the 293 strain to the sugar added in the middle of culture.

Further, another finding of the present inventors indicates that it becomes possible to have the 293 cells secrete a further large amount of useful protein by starting the culture of the 293 strain in a medium containing calcium ions in a low concentration and adding a calcium salt together with a sugar in a certain stage of the culture. According to this another finding, proliferation of the cells is substantially suppressed and secretion of the useful protein is further promoted by the addition of the calcium. Therefore, it becomes possible to obtain the useful protein in a larger amount.

Thus, according to another embodiment of this invention, there is provided a process of production of a useful protein by culturing mammalian cell in a suspension state, wherein the improvement is in that the mammalian cell is a human embryonal kidney cell-derived 293 strain which is introduced with a useful protein-expressing gene, and in that the process comprises (i) starting the culture in a culture medium having a calcium ion concentration of 0.002 to 0.25 mM at a cell density of $5 \times 10^4$ to $5 \times 10^5$ cells/ml, (ii) proliferating the cells until the cell density in the culture fluid becomes three times or still higher than the inoculum cell density and comes to a range of $5 \times 10^5$ to $5 \times 10^6$ cells/ml, (iii) adding a sugar and a calcium into the culture fluid so that the increase of the cell density is substantially suppressed and the production of the useful protein is maintained, (iv) continuing the culture until the substantial increase of the concentration of the useful protein in the culture vessel does not come to be recognized, and then stopping the culture, and (v) taking out the culture fluid from the culture vessel and recovering the useful protein from the culture fluid.

The process of this invention is described more clearly below.

A cell line which is used in this invention is a transformant of the human embryonal kidney cell-derived 293 strain. This human embryonal kidney cell-derived 293 strain itself is known and, for example, deposited with ATCC under the accession number of CRL 1573, and therefore, is a cell line easy to get. In the process of this invention, a transformant obtained by introducing a useful protein-expressing gene into this 293 strain is cultured. This transformant of the 293 strain is a cell line wherein a gene was integrated so as to secrete an object protein. As useful object proteins, there can be mentioned proteins having various physiological properties. Useful proteins can be Gla proteins. Such Gla proteins are proteins having a Gla-domain, and specifically, examples are Protein C, activated Protein C, the Factor VII, Factor IX, Factor X, prothrombin, osteocalcin, Protein S, Protein Z, etc.

Particularly, the process of this invention is suitable for production of human Protein C, activated human Protein C, proteins having a physiological activity similar to them, or precursor proteins thereof. In the above, the precursor proteins mean ones which can be converted to human Protein C, activated human Protein C or proteins having a physiological activity similar to them by processings such as partial conversion, cleavage or deletion of the proteins.

The 293 strain expressing human Protein C or activated human Protein C is known per se, and the known transformants of the 293 strain are suitable as a cell line applicable for the process of this invention (for example, refer to U.S. Pat. No. 4,968,626 and EP 319944A2).

In the process of this invention, the transformant of the 293 strain mentioned above is cultured in a suspension state by a fed-batch method. In this occasion, a culture vessel to be used can be a vessel used in a usual batch culture, for example, a tank-type vessel. This transformant of the 293 strain is an adherent cell line, and hence, in order to maintain the cells in a suspension state in the culture vessel, the culture is carried out under stirring. Therefore, the culture is carried out by a usual stirred culture method.

The culture vessel is equipped with oxygen supply means together with stirring means. Oxygen can be supplied by bubbling of oxygen gas or air, or using gas-permeable porous tube, or by any other suitable means. As a porous tube, a Teflon ® tube or a silicone rubber tube is recommended. Oxygen is so supplied that dissolved oxygen can be maintained at about 2 to 5 ppm, preferably about 3 ppm, in the culture fluid.

Many kinds of culture media can be used for the process of this invention. Synthetic media known well and used widely can be used as basal media. As basal media, there can be mentioned RPMI-1640 (RPMI1640 medium), MEM (Eagle's minimum essential medium), DME (Dulbecco's modification of Eagle's medium), Isocove (Isocove's modification of Dulbecco's medium), 199 (199 medium), F10 (Ham's F10 medium), F12 (Ham's F12 medium), etc. All these basal media are commercially available and easy to get.

These media are used alone or in an appropriate combination of two or more, and various amino acid, vitamins, inorganic salts and glucose can be added additionally to make a modified medium.

In the process of this invention, a serum-free medium can be used, and the use of it is desirable for lowering medium costs. Although media containing serum can also be used, medium cost is generally high and hence, the advantage of addition of serum is small. Even when serum is added, the amount is preferably at most 5 vol %, more preferably at most 3 vol %.

It is industrially advantageous to carry out the process of this invention using a serum-free medium. In this occasion, "eRDF" medium can be used as a basal medium. This eRDF medium is a medium obtained by mixing RPMI-1640 medium, Ham's F12 medium and Dulbecco's modification of Eagle's medium in a ratio of 2:1:1 and further adding glucose, amino acids, etc., and is a medium known per se (refer to Monoclonal Antibodies: Production and Application, pp. 107–141, Alan R. Liss, Inc. 1989, and Hiroki Murakami, "Serum-Free Media Used for Cultivation of Hybridomas").

The basal media mentioned above or the eRDF medium usually contain about 0.3 mM or more, particularly about 0.5 mM to about 2 mM, of calcium ion.

In the process of this invention, it is desirable to add into the basal medium, further, growth factors, for example, ITES (a mixture of insulin, transferrin, ethanolamine and sodium selenite).

As stated above, it is one of preferred embodiments of the process of this invention to start culture using a medium containing calcium ion in a low concentration. Such a medium containing calcium ion in a low concentration (hereafter sometimes referred to as "low Ca medium") means a medium containing 0.0025 to 0.25 mM, preferably 0.05 to 0.2 mM of calcium ions.

Since the basal media mentioned above contain, in many cases, calcium ion in a concentration higher than those of the low Ca media, a medium containing no calcium ion or containing a calcium ion in an extremely low content should be specially prepared for producing a low Ca medium for the preferred embodiment. Thus, it is desirable to use a medium prepared using eRDF composition in a low calcium concentration as a basal medium.

In the fed-batch culture method of this invention, culture is started by inoculating a transformant of the 293 strain in a medium in a culture vessel. In this occasion, it is advantageous to inoculate the cells in a density of the range of $5 \times 10^4$ to $5 \times 10^5$ cells/ml, preferably in a density of the range of $8 \times 10^4$ to $3 \times 10^5$ cells/ml. When the inoculating cell density is lower than the range above, it takes long time to reach a desired density and nutrients are considerably consumed before the density is gained, and consequently, it becomes difficult to obtain a desired useful protein efficiently. On the other hand, in the case that an inoculum cell density is higher than the range above, it becomes necessary to prepare a lot of cells before the culture is started, which is economically disadvantageous.

Generally, when culture is started and continued, the cell density gradually increases and, therewith, the concentration of the useful protein, too, increases, and after further continuation of the culture, the cell density reaches at a maximum value. The cells die after that, and the culture terminates.

In the process of this invention, a sugar is added in the culture fluid at any point of culture period when, after the start of culture, the cell density becomes three times or still higher than the inoculum density and reaches the range of $5 \times 10^5$ to $5 \times 10^6$ cells/ml. It is particularly preferable to add the sugar at any point of culture period when the cell density becomes four times or still higher than the inoculum cell density and when the cell density is in the range of $8 \times 10^5$ to $3 \times 10^6$ cells/ml.

Further, it is desirable to determine the time of the addition of the sugar upon monitoring the cell density and the sugar concentration in the culture fluid. Namely, it is advantageous to add a sugar between the time when the sugar concentration in the culture fluid becomes 70% or less, preferably 50% or less, than the initial concentration and the time when the sugar concentration becomes 0.2 g/l, preferably 0.3 g/l.

In the process of this invention, it is adequate to make the addition of a sugar in the middle of culture in the range above upon monitoring the cell density and the sugar concentration. The amount of a sugar to be added depends on the cell density and sugar concentration in the culture fluid at the time of addition, the culture period or calcium ion concentration, etc. However, the sugar is generally so added that the sugar concentration in the culture fluid can become 1 to 7 g, preferably 2 to 5 g, per liter of the culture fluid.

As the sugar to be added, there can be mentioned glucose, mannose or fructose, etc., but glucose or mannose is preferable, and glucose is the most desirable.

The number of the times of addition of the sugar can be once or twice or more so long as the addition is made in the course of the time above. However, the advantage of repeated addition of a sugar is small, and the object is fully attained by adding once.

A preferred embodiment of the process of this invention is to start a culture using the low calcium medium mentioned above, and, as stated above, add a specific amount of a sugar into the culture fluid in the middle of the culture and add a calcium salt.

In this case, it is advantageous to add a sugar and a calcium salt into the culture fluid so that the cell density in the culture vessel is controlled in the range of ±50% (−50% to +50%) preferably in the range of ±30% (−30% to +30%) of the standard maximum cell density. By such addition of the sugar and calcium salt, the increase of cell density is substantially suppressed and the culture period is remarkably prolonged without any decrease of the secretion of a useful protein. The "standard maximum cell density" means the value of a maximum density which reaches in the culture fluid when a simple batch culture is carried out under the same culture conditions as a fed-batch culture in which sugar and calcium salt are added in the middle of culture, and it can easily be determined by a preliminary experiment.

The time of addition of the calcium may be in the range almost the same as that of the sugar, but it is unnecessary to add the calcium together with the sugar at the same time. Preferably, the calcium salt is added in such an amount that the calcium ion concentration in the culture fluid becomes 0.3 to 3 mM at any time between the time when the sugar. concentration in the culture fluid becomes 50% or less of the sugar concentration at the time of the start of culture and the time prior to the lapse of two days after the addition of the sugar.

When a culture is, thus, started using a low calcium medium, and a sugar and a calcium are added in the middle of the culture, the increase of cell density is substantially suppressed after the addition of them and production of a useful protein is maintained for a long period, and hence, a culture fluid containing the useful protein in a high concentration can be obtained.

The addition of a calcium salt is advantageously conducted at any time between the time when the sugar concentration in the culture fluid becomes 70% or less of the sugar concentration at the time of the start of culture and the time of addition of the sugar. It can be made with the addition of the sugar at a time. It is still preferable to add the calcium such that the calcium ion concentration in the culture fluid becomes 0.5 to 2.5 mM.

Calcium salts to be added can be ones soluble in water, for example, calcium chloride ($CaCl_2$) or calcium nitrate ($Ca(NO_3)_2$).

Although the cells tend to aggregate and form clumps by the addition of the calcium salt, the size of the clumps is not so big as to cause substantial hindrance against the maintenance of secretion of the useful protein, since the increase of the cell density is substantially suppressed.

Thus in the culture in the process of this invention, the pH of the culture fluid is maintained in the range of 6.5 to 7.8, preferably in the range of 6.6 to 7.5.

It is desirable that culture is continued while monitoring the concentration of the useful protein in the culture fluid and the culture is stopped when the substantial increase of the concentration of the useful protein cannot be recognized.

After the completion of the culture, the culture fluid is taken out from the vessel and the cells are separated and removed. For the separation of the cells, a means such as filtration or centrifugation is adopted. For the recovery of the useful protein from the culture fluid from which the cells have been removed, a suitable method is selected depending on the kind of the useful protein. For example, immunological adsorption, ion exchange resin adsorption or the like is employed.

When the useful protein is human Protein C, activated human Protein C, a protein having a physiological activity similar to that of them, or a precursor protein thereof, the useful protein can, for example, be recovered by a separation method using a monoclonal antibody disclosed in U.S. Pat. No. 4,902,614, or a separation method using an ion exchange resin disclosed in U.S. Pat. No. 4,981,852.

According to the process of this invention, it is possible to obtain a culture fluid containing a useful protein in a high concentration and to decrease extremely the amount of the medium consumed per the obtained useful protein by the culture of a transformant of the 293 strain. Thus, it is possible to lower the costs of the production of a useful protein significantly since the consumption of an expensive medium is lowered and sugars and calcium salts to be added in the middle of culture are extremely inexpensive.

The following are a consumption of the medium per the unit amount (mg) of the useful protein in a perfusion continuous culture method, a simple batch culture method, a conventional fed-batch culture method and the fed-batch culture method according to the invention.

Culture methods:
(A) A perfusion continuous culture method (EP 0343635A2)
(B) A simple batch culture method (a fresh medium, a sugar and a calcium salt were not added at all in the middle of the culture)
(C) A conventional fed-batch culture method (a fresh medium was added in the middle of culture)
(D) A fed-batch culture method of the invention (a sugar and a calcium salt were added in the middle of the culture)

The premise for the calculation:
(1) Cell strain
   The human Protein C-producing 293 strain used in Example 1
(2) Useful protein
   Human Protein C (PC)
(3) Medium
   ITES eRDF containing 0.1 mM calcium ions
(4) Volume of the culture vessel 350 ml
(5) Perfusion continuous culture method
   It is assumed that after the PC concentration reaches maximum, the concentration is maintained during the culture period (perfusion rate is 300 ml/day).
(6) Culture period
   6 months (in the case of batch culture method, the initial batch culture is carried out until the PC concentration reaches maximum, and it is assumed that the batch is repeated taking the number of days needed for the initial batch culture as the repeating unit.)
(7) Maximum PC concentration in the culture fluid and the number of days of culture
   As shown in the Table 2.
(8) Amount of the medium used and the amount of PC produced
   As shown in the Table 3.

TABLE 2

| Culture method | Maximum PC concentration in the fluid (μg/ml) | Culture period needed to get the maximum PC concentration (days) |
| --- | --- | --- |
| (A) Perfusion continuous culture method | 17.9 | 6 |
| (B) Simple batch culture method | 9.0 | 11 |
| (C) Conventional fed-batch culture method | 11.0 | 7 |
| (D) Fed-batch culture method (this invention) | 102.9 | 28 |

TABLE 3

| Culture method | Number of repeat of culture | Amount of the medium used (ml) | Amount of PC produced (mg) | Medium used per unit amount of PC (ml/mg) |
|---|---|---|---|---|
| (A) Perfusion continuous culture method | 1 | 53,800 | 958 | 56.2 |
| (B) Simple batch culture method | 16 | 4,800 | 43.2 | 111.1 |
| (C) Conventional fed-batch culture method | 25 | 7,500 | 82.5 | 90.9 |
| (D) Fed-batch culture method (this invention) | 6 | 1,800 | 185.2 | 9.7 |

As apparent from the Tables above, it is possible, according to the process of this invention, to produce a protein with an extremely small amount of the medium. A usual fed-batch culture method (C) is generally a method of adding a fresh medium, but in the process of this invention, it is possible to lower the amount of the medium used more greatly than this method (C).

DESCRIPTION OF THE PREFERRED EMBODIMENT(S)

EXAMPLES

The process of this invention is specifically described below according to examples.

Example 1

1) Medium

As a basal medium, eRDF (a mixture of RPMI-1640, DME and F12 in a ratio of 2:1:1 enriched with amino acids, glucose, etc.) deprived of calcium salts (calcium chloride and calcium nitrate) except calcium pantothenate, [hereafter referred to as low Ca eRDF] was used. Insulin, tranaferin, ethanolamine and sodium selenite (ITES) were added as growth factors. The concentration of ITES are 9 μg/ml, 10 μg/ml, 10 μM and 20 μM, respectively.

2) Culture method and results

The culture medium was put in a 350-ml culture vessel autoclave-sterilized in advance so that the net culture volume became about 300 ml, and therein was inoculated a Protein C-producing strain 293/21-26 obtained by introducing a gene encoding the amino acid sequence of human Protein C into the 293 strain derived from a human embryonal kidney cell obtained from ATCC using the method disclosed in WO92/13079.

Oxygen gas was introduced into the gaseous phase above the culture fluid in the culture vessel to maintain the dissolved oxygen concentration at 3 ppm.

The culture fluid in the culture vessel was held at 37° C. The culture vessel was equipped with a marine type agitating impeller and the agitation speed was 40 rpm.

Eight days after the culture started, 1.0 g of D-glucose and 32.6 mg of calcium chloride dihydrate were added in the form of 3 ml of a mixed aqueous solution (the concentration of each component in the culture fluid was 19 mM for glucose and 0.74 mM for calcium chloride).

Figure 1:
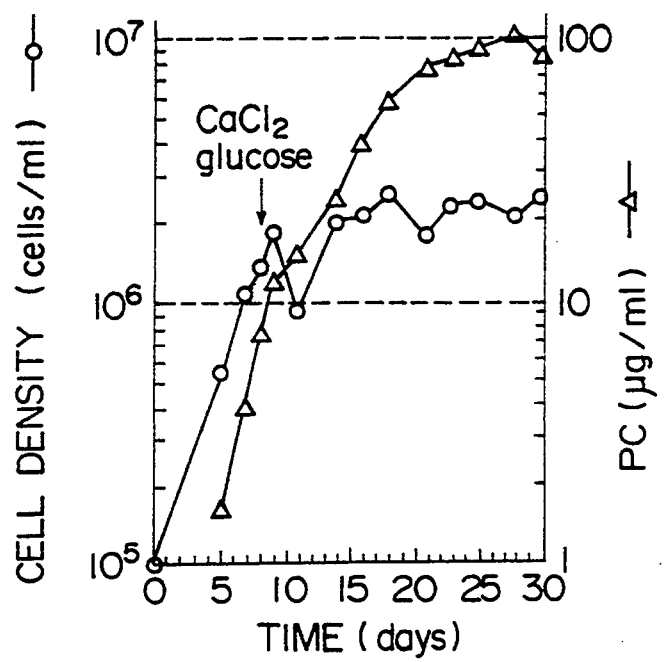
FIG. 1 is a drawing showing the results of the culture of Example 1.

Culture results are shown in FIG. 1. In FIG. 1, PC denotes human Protein C (this applies to the following Examples and Comparative Examples). The cell line, the medium and the additives in the middle of the culture used in this example are as follows.

Cell: 293/21-26
Medium: 0.1 mM $CaCl_2$+low Ca eRDF+ITES
Additives in the middle of the culture:
 1 g of glucose+32.6 mg of calcium chloride dihydrate (3 ml of a mixed aqueous solution)

Comparative Example 1

Figure 2:
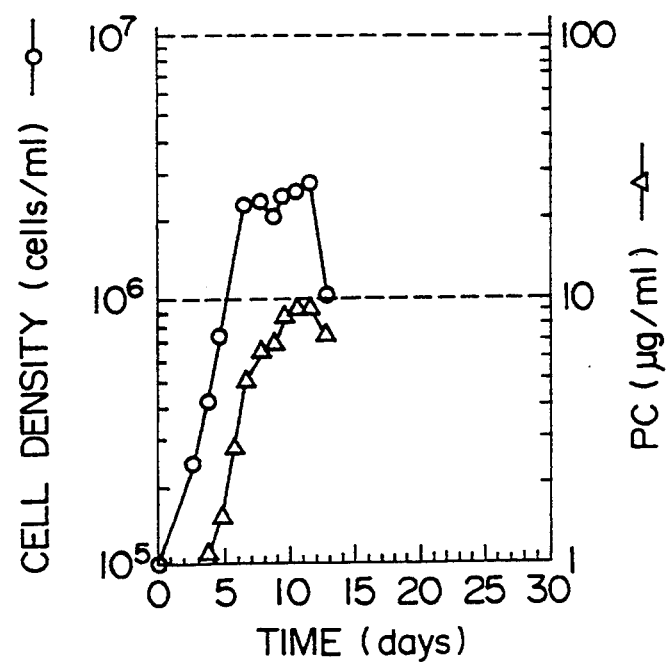
FIG. 2 is a drawing showing the results of the culture of Comparative Example 1.

The same operations as in Example 1 were carried out except that any addition in the middle of the culture was not made. Culture results are shown in FIG. 2. The cell line, the medium and the additives in the middle of the culture used in this example are as follows.

Cell: 293/21-26
Medium: 0.1 mM $CaCl_2$+low Ca eRDF+ITES
Additives in the middle of the culture: None

Comparative Example 2

Figure 3:
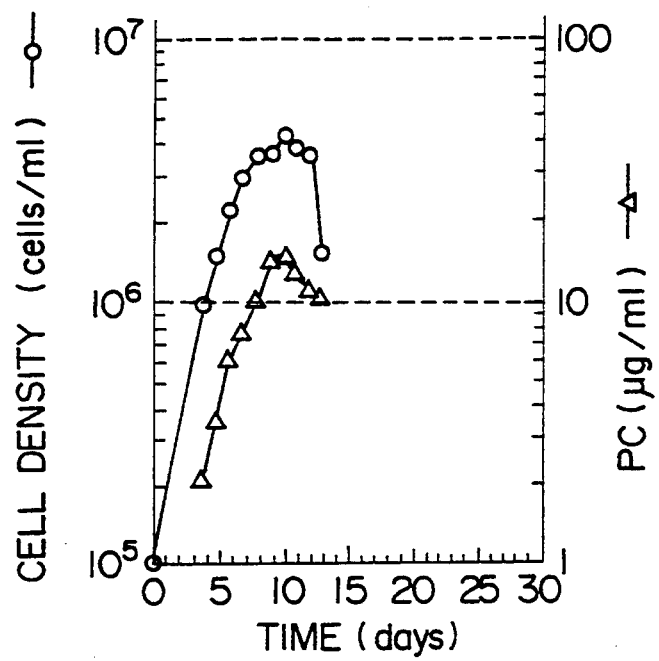
FIG. 3 is a drawing showing the results of the culture of Comparative Example 2.

The same operations as in Comparative Example 1 were carried out except that eRDF (calcium ion concentration 0.74 mM) was used as a basal medium. Culture results are shown in FIG. 3. The cell line, the medium and the additives in the middle of the culture used in this example are as follows.

Cell: 293/21-26
Medium: eRDF+ITES
Additives in the middle of the culture: None

Example 2

Figure 4:
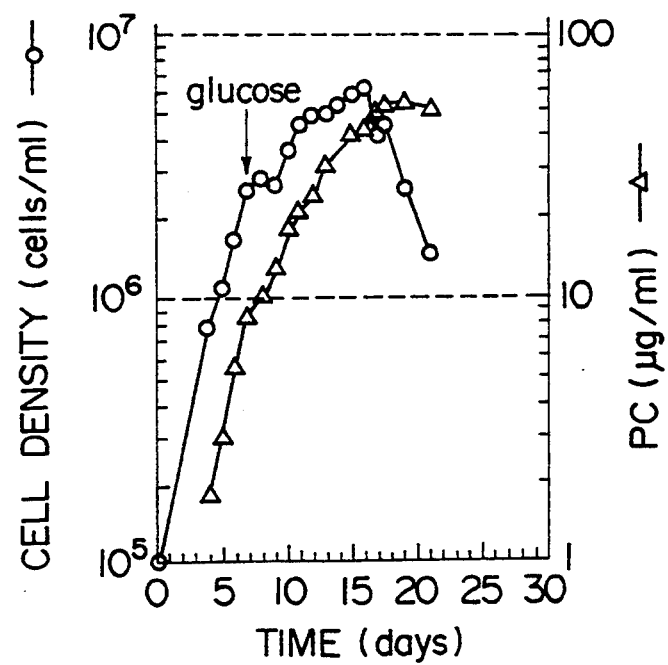
FIG. 4 is a drawing showing the results of the culture of Example 2.

The same operations as in Example 1 were carried out except that only glucose was used as an additive in the middle of the culture. Culture results are shown in FIG. 4. The cell line, the medium and the additive in the middle of the culture used in this example are as follows.

Cell: 293/21-26
Medium: 0.1 mM $CaCl_2$+low Ca eRDF+ITES
Additives in the middle of the culture:
 1 g of glucose (3 ml of an aqueous solution)

Example 3

Figure 5:
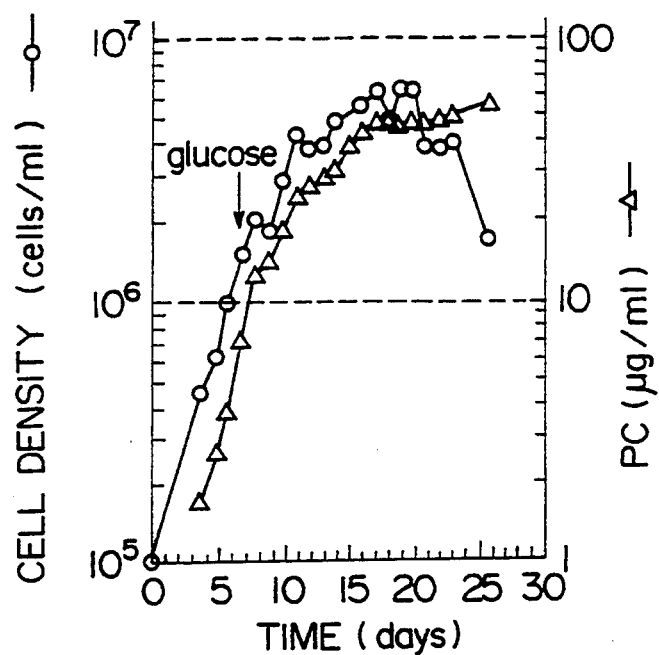
FIG. 5 is a drawing showing the results of the culture of Example 3.

The same operations as in Comparative Example 3 were carried out except that eRDF was used as a basal medium. Culture results are shown in FIG. 5. The cell line, the medium and the additives in the middle of the culture used in this example are as follows.
Cell: 293/21-26
Medium: eRDF+ITES
Additives in the middle of the culture:
  1 g of glucose (3 ml of an aqueous solution)

Comparative Example 3

Figure 6:
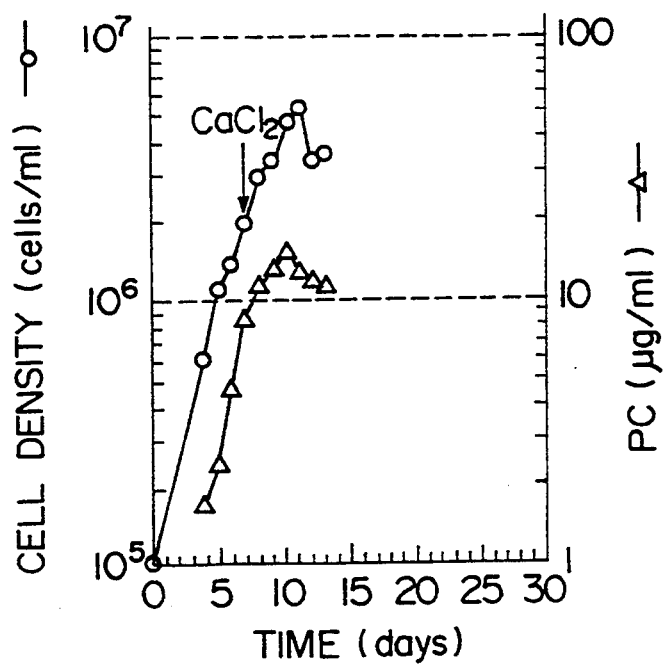
FIG. 6 is a drawing showing the results of the culture of Comparative Example 3.

The same operations as in Example 1 were carried out except that only calcium chloride was used as an additives in the middle of the culture. Culture results are shown in FIG. 6. The cell line, the medium and the additive in the middle used in this comparative example are as follows.
Cell: 293/21-26
Medium: 0.1 mM $CaCl_2$+low Ca eRDF+ITES
Additives in the middle of the culture:
  32.6 g of calcium chloride dihydrate (3 ml of an aqueous solution)

Comparative Example 4

Figure 7:
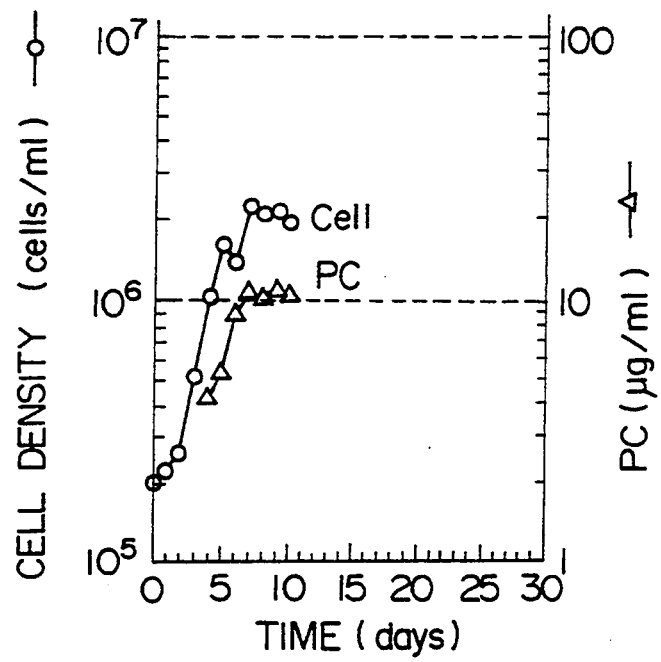
FIG. 7 is a drawing showing the results of the culture of Comparative Example 4.

The same operations as in Comparative Example 1 were carried out except that the initial culture volume was 150 ml, and a fresh medium was fed at a constant speed (6.25 ml/hr) over a period from the fourth day to the fifth day of the culture to make the culture volume 300 ml. The results are shown in FIG. 7.

The results of Examples 1 to 3 and Comparative Examples 1 to 4 are summarized together in the following Table 4.

TABLE 4

| | Calcium concentration in the initial medium (mM) | Additive | Maximum cell density ($\times 10^6$ cells/ml) | Maximum PC concentration ($\mu g/ml$) |
|---|---|---|---|---|
| Ex. 1 | 0.10 | glucose + calcium chloride | 2.4 | 103 |
| Comp. Ex. 1 | 0.10 | none | 2.6 | 9.0 |
| Comp. Ex. 2 | 0.74 | none | 4.3 | 15.3 |
| Ex. 2 | 0.10 | glucose | 6.3 | 54.8 |
| Ex. 3 | 0.74 | glucose | 6.3 | 55.0 |
| Comp. Ex. 3 | 0.10 | calcium chloride | 5.4 | 15.3 |
| Comp. Ex. 4 | 0.10 | fresh medium | 2.3 | 10.1 |

Comparative Example 5

Figure 8:
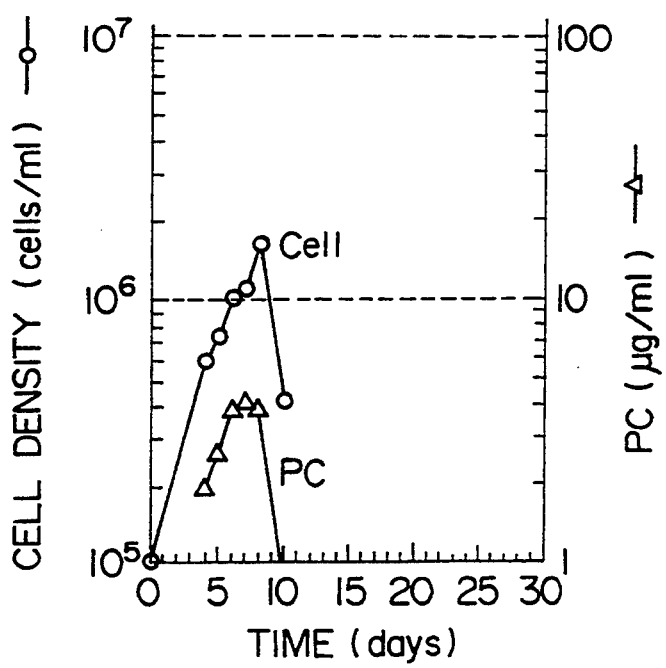
FIG. 8 is a drawing showing the results of the culture of Comparative Example 5.

The same operations as in Comparative Example 1 were carried out except that a human Protein C-producing cell line BHK/J3-26 strain was used in place of the 293/21-26. This BHK/J3-26 is a cell line obtained by introducing a gene encoding the amino acid sequence of human Protein C into the BHK cell strain according to the method described below. The results are shown in FIG. 8.

Comparative Example 6

Figure 9:
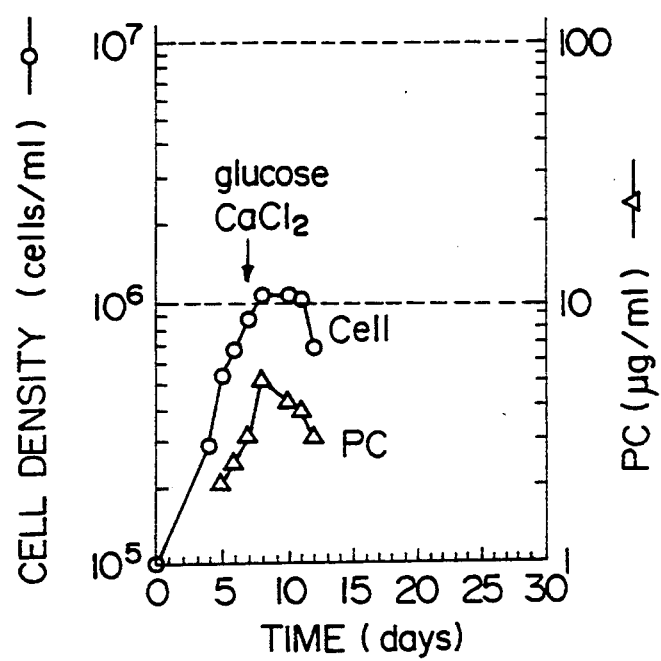
FIG. 9 is a drawing showing the results of the culture of Comparative Example 6.

The same operations as in Example 1 were carried out except that the BHK/J3-26 cell line mentioned in Comparative Example 5 was used in place of the 293/21-26, and the following additive in the middle of the culture was used. The results are shown in FIG. 9.
  0.5 g of glucose+32.6 mg of $CaCl_2.2H_2O$ (3 ml of a mixed aqueous solution)

In the above Examples and Comparative Examples, 293/21-26 and BHK/J3-26, respectively, were prepared by following methods.

(A) Preparation of 293/21-26

293 Strain was transformed with plasmid TZm5-PC9002 having DNA sequence encoding amino acid sequence of human protein C described in page 25 of WO 92/13079 according to the method described also in the WO 92/13079 to obtain human protein C-producing cell line, 293/21-26.

(B) Preparation of BHK/J3-26

Plasmid TZm1D-9002 having DNA sequence encoding amino acid sequence of human protein C was inserted into BHK strain, and plasmid ZmB4 KEX2 having DNA sequence encoding amino acid sequence of KEX2 (preparation method is described below) and the above TZm5-PC9002 were co-transfected to obtain BHK/J3-26.

Methods of preparing TZm1D-9002 and ZmB4 KEX2

Figure 10:
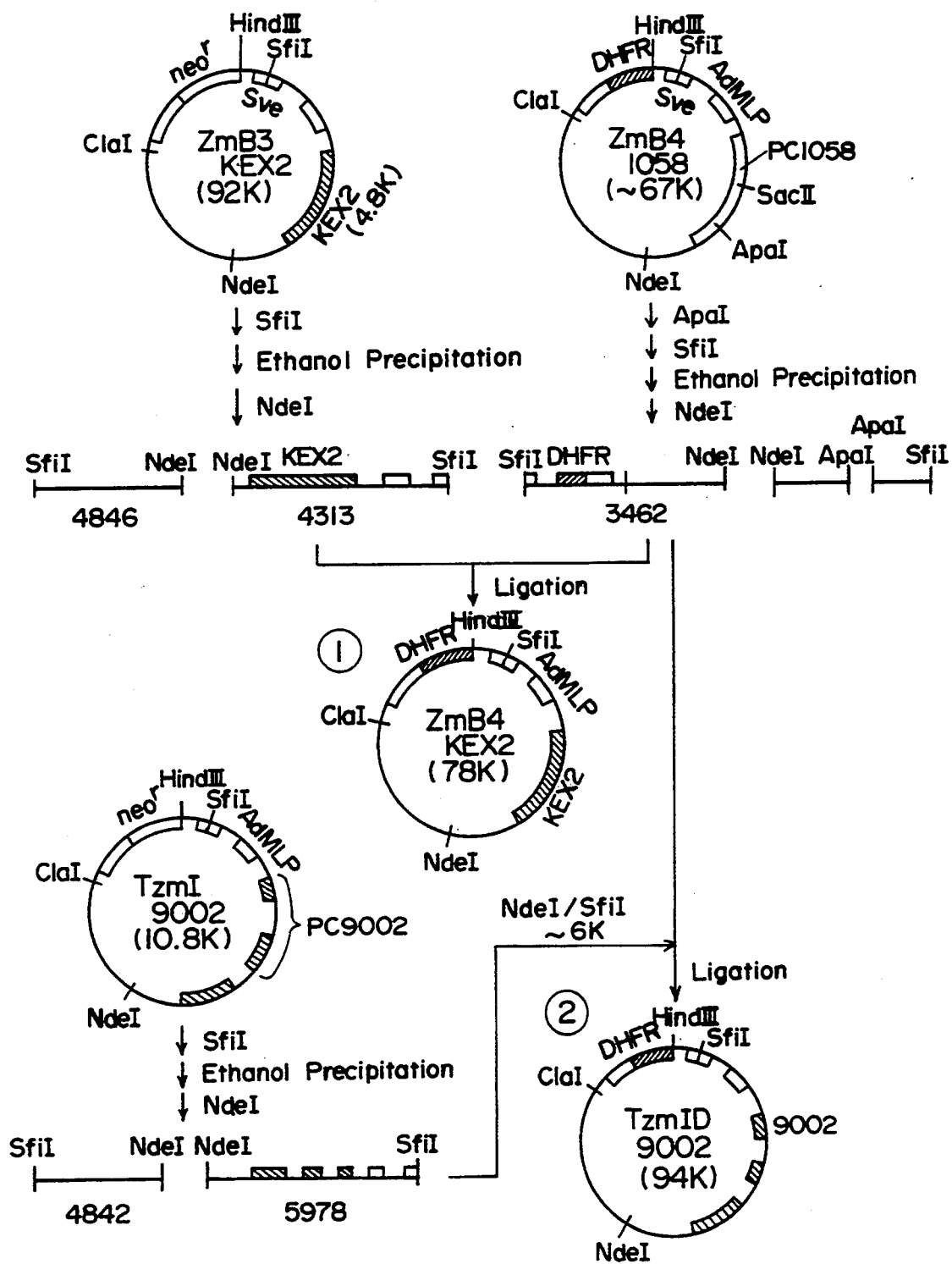
FIG. 10 is a drawing showing the outline of the preparation procedures for BHK/J3-26.

TZm1D-9002 and ZmB4 KEX2 were prepared from ZmB3 KEX2 and ZmB4 1058 (preparation methods are described below) by the following procedures. The procedures are outlined in FIG. 10.

ZmB3 KEX2 was digested with SfiI and NdeI, and KEX2 gene-containing DNA fragment of 4.31 Kbp was isolated (K-fragment). Further, ZmB4 1058 was digested with ApaI, SfiI and NdeI, and DHFR gene-containing DNA fragment of 3.46 Kbp was isolated (D-fragment). K-fragment and D-fragment were ligated to obtain ZmB4 KEX2.

Further, the TZm1D-9002 was digested with SfiI and NdeI, and human protein C-containing DNA fragment of 5.98 Kbp was isolated (P-fragment). P-fragment and D-fragment were ligated to obtain TZm1D-9002.

Method of preparing ZmB3 KEX2

Plasmid KEX/Zem 229 described in EP 0319944A2 was digested with Bam HI, and KEX2 gene-containing DNA fragment was isolated (D'-fragment). Further, plasmid ZmB3 described in WO91/09960 was digested with Bam HI, and the resultant fragment and D'-fragment were ligated to obtain ZmB3 KEX2.

Method of preparing ZmB3 1058 pDX/PC1058 described in EP 0266190 was digested with EcoRI, and human protein C-containing DNA fragment was isolated (P'-fragment). Further, plasmid PC962/ZMB-4 described in WO 91/09960 was digested with EcoRI, and DNA fragment not containing human protein C-encoding DNA was isolated (Z-fragment). P'-fragment and Z-fragment were ligated to obtain ZmB4 1058.

We claim:

1. In a process for the production of a protein by culturing mammalian cells in a suspension state, the improvement comprising culturing as the mammalian cells a human embryonal kidney cell-derived 293 strain which is transformed with a gene encoding the protein, and the improvement further comprising culturing the mammalian cell using a process which comprises
  (a) starting the culture of the mammalian cells in a culture medium contained in a culture vessel at a cell density of $5\times10^4$ to $5\times10^5$ cells/ml, (b) adding a sugar to the culture vessel to give a sugar concentration of 1 to 7 g/l at any time after the cell density of the mammalian cells in the culture vessel has become three times higher than the starting cell density and when the cell density is in a range of $5 \times 10^5$ to $5 \times 10^6$ cells/ml, (c) continuing the culture until the concentration of the protein is no longer substantially increasing, while maintaining the pH of the culture fluid, and then stopping the culture, and (d) taking out culture fluid from the culture vessel and recovering the protein from the culture fluid.

2. The process according to claim 1 wherein the culture is started in the culture medium having a calcium ion concentration of 0.002 to 0.25 mM.

3. The process according to claim 1 wherein the pH of the culture fluid is maintained in a range of 6.5 to 7.8.

4. The process according to claim 1 wherein the sugar is added to give a concentration of 2 to 5 g/l.

5. The process according to claim 1 wherein the sugar is added at any time between the time when the sugar concentration in the culture fluid is 50% or less of the sugar concentration at the start of the culture and the time when the sugar concentration in the culture fluid is 0.2 g/l.

6. The process according to claim 2 wherein calcium is added in such an amount that the calcium ion concentration in the culture fluid becomes 0.3 to 4 mM at any time between the time when the sugar concentration in the culture fluid is 50% or less of the sugar concentration at the start of culture and the time prior to the lapse of two days after the addition of the sugar.

7. The process according to claim 1 wherein the sugar is at least one member selected from the group consisting of glucose, mannose and fructose.

8. The process according to claim 1 wherein the culture is carried out in a serum-free medium.

9. The process according to claim 8 wherein the serum-free medium is prepared using eRDF (enriched RDF) medium as a basal medium.

10. The process according to claim 1 wherein the protein is a Gla protein.

11. The process according to claim 1 wherein the protein is human Protein C or activated human Protein C.

12. The process according to claim 1 wherein no additional fresh medium is added into the culture vessel during the culture.

13. In a process for the production of a protein by culturing mammalian cells in a suspension state, the improvement comprising culturing as the mammalian cells a human embryonal kidney cell-derived 293 strain which is transformed with a gene encoding the protein, and the improvement further comprising culturing the mammalian cells using a process which comprises (i) starting the culture of the mammalian cells in a culture medium contained in a culture vessel having a calcium ion concentration of 0.002 to 0.25 mM at a cell density of $5 \times 10^4$ to $5 \times 10^5$ cells/ml, (ii) proliferating the cells until the cell density in a culture fluid becomes three times or higher than the starting cell density in a range of $5 \times 10^5$ to $5 \times 10^6$ cells/ml, (iii) adding a sugar and calcium to the culture fluid so that an increase of the cell density is substantially suppressed and production of the protein is maintained, (iv) continuing the culture until the concentration of the protein in the culture vessel is no longer substantially increasing, and then stopping the culture, and (v) taking out the culture fluid from the culture vessel and recovering the protein from the culture fluid.

14. The process according to claim 13 wherein the addition of the sugar and the calcium to the culture vessel is carried out so that the cell density in the culture vessel is inhibited to be in the range of ±50% of the standard maximum cell density.

15. The process according to claim 13 wherein the pH of the culture fluid is maintained in the range of 6.5 to 7.8.

16. The process according to claim 13 wherein the sugar is added to give a concentration of 1 to 7 g/l, preferably 2 to 5 g/l.

17. The process according to claim 13 wherein the sugar is added at any time between the time when the sugar concentration in the culture fluid is 50% or less of the sugar concentration at the start of the culture and the time when the sugar concentration in the culture fluid is 0.2 g/l.

18. The process according to claim 13 wherein the calcium is added in an amount such that the calcium ion concentration in the culture vessel becomes in the range of 0.3 to 4 mM at any time between the time when the sugar concentration in the culture vessel becomes 50% or less of the sugar concentration at the time of the start of culture and the time prior to the lapse of two days after the addition of the sugar.

19. The process according to claim 13 wherein the sugar is at least one member selected from the group consisting of glucose, mannose and fructose.

20. The process according to claim 13 wherein the culture is carried out in a serum-free medium.

21. The process according to claim 20 wherein the serum-free medium is the one prepared using eRDF (enriched RDF) medium as a basal medium.

22. The process according to claim 13 wherein the useful protein is a Gla protein.

23. The process according to claim 13 wherein the useful protein is human Protein C, activated human Protein C, a protein having the similar physiological activity to them, or a precursor protein thereof.

24. The process according to claim 13 wherein a fresh medium is not additionally added into the culture vessel during the culture.

* * * * *